United States Patent
Kurihara et al.

[11] Patent Number: 6,162,614
[45] Date of Patent: Dec. 19, 2000

[54] SUGAR ESTER DERIVATIVES, REAGENTS FOR MEASUREMENT OF HYDROLASE ACTIVITY AND METHODS FOR MEASUREMENT OF HYDROLASE ACTIVITY

[75] Inventors: Toshio Kurihara; Toshiyuki Nishio; Hisao Yamamoto; Minoru Kamimura, all of Yaizu; Shinichi Teshima, Tsuruga; Tsuneo Hanyu, Tsuruga; Shigenori Emi, Tsuruga, all of Japan

[73] Assignee: Toyo Boseki Kabushiki Kaisha, Osaka, Japan

[21] Appl. No.: 07/975,167

[22] Filed: Nov. 12, 1992

Related U.S. Application Data

[63] Continuation of application No. 07/802,695, Dec. 5, 1991, which is a continuation of application No. 07/367,137, Jun. 16, 1989.

[30] Foreign Application Priority Data

Jun. 17, 1988 [JP] Japan .................................. 63-150527

[51] Int. Cl.$^7$ ...................................................... C12Q 1/34
[52] U.S. Cl. ................. 435/18; 435/19; 435/22; 536/17.8
[58] Field of Search ............................. 536/17.8; 435/18, 435/19, 22

[56] References Cited

U.S. PATENT DOCUMENTS

| | | |
|---|---|---|
| 4,102,747 | 7/1978 | Driscoll et al. . |
| 4,145,527 | 3/1979 | Burns et al. . |
| 4,147,860 | 4/1979 | Farnham et al. . |
| 4,472,499 | 9/1984 | McCroskey ................................ 435/18 |
| 4,709,020 | 11/1987 | Bausher et al. ......................... 536/17.8 |
| 4,794,078 | 12/1988 | Blair .......................................... 435/18 |

FOREIGN PATENT DOCUMENTS

| | | |
|---|---|---|
| 85348 | 8/1983 | European Pat. Off. . |
| 0263435 | 4/1988 | European Pat. Off. . |

OTHER PUBLICATIONS

Morrison et al., *Organic Chemistry* 2nd Ed., Allyn & Bacon, Inc. pp 790–791 (1966).
Fleisher, M., "An automated, fluorometric procedure for determining serum lipase," Clin Chem 17., 417–422 (1971).
Fuji Rebio et al., "Method for Measuring Lipase Activity", Patent Abstracts of Japan, vol. 10, No. 101, Apr. 17, 1986.
Junko Makise et al., "Kinetic Rate Assay of Urinary N–Acetyl–β–D–Glucosaminidase with 2–Chloro–4–Nitrophenyl–N–Acetyl–β–D–Glucosaminide as Substrate", Clinical Chemistry, vol. 34, No. 10, pp. 2140–2143 (1988).
Georg E. Hoffman et al., "An Enzymatic Method for Calibration of Serum Lipase Assays", Clinical Chemistry, vol. 32, No. 3, pp. 545–547 (1986).

*Primary Examiner*—M. Patrick Woodward
*Attorney, Agent, or Firm*—Foley & Lardner

[57] ABSTRACT

A sugar ester derivative of the general formula (I)

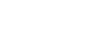

(I)

wherein G stands for a group of the formula (A)

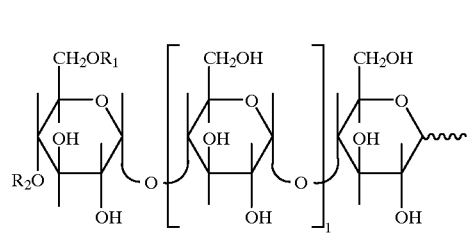

(A)

or a group of the formula (B)

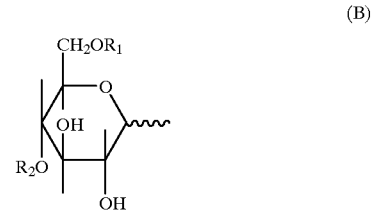

(B)

wherein λ means 0 or 1; at least one of $R_1$ and $R_2$ means an ester residue of a saturated or unsaturated fatty acid having 1–30 carbon atoms and the other group means hydrogen atom or acetyl group, and $R_3$ means a group of the formula (C)

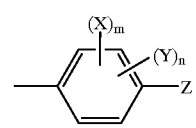

(C)

wherein X means a halogen atom, m means an integer of 0 to 4, Y means hydroxy group, an alkoxy group, a carboxyl group or sulfonic acid group, n means 0 or 1 and Z means nitro group or nitrovinyl group and its use.

The sugar ester derivative of the general formula (I) is useful as a substrate for the measurement of lipase or esterase activities, and the reagents and the methods for measuring lipase or esterase activities which comprise said sugar ester derivative as the substrate are excellent in terms of reproducibility and sensitivity and enable the measurement of lipase or esterase activities in accordance with rate-assay method by an easy procedure.

8 Claims, No Drawings

SUGAR ESTER DERIVATIVES, REAGENTS FOR MEASUREMENT OF HYDROLASE ACTIVITY AND METHODS FOR MEASUREMENT OF HYDROLASE ACTIVITY

This application is a continuation of U.S. application Ser. No. 07/802,695 filed Dec. 5, 1991; which is a continuation of Ser. No. 07/367,137 filed Jun. 16, 1989.

BACKGROUND OF INVENTION

This invention relates to novel sugar ester derivatives, reagents for measuring activities of lipases or esterases which comprise said sugar ester derivatives as the substrate and methods for measuring activities of lipases or esterases.

Diagnosis of various diseases such as pancreatic diseases is conducted by measuring activities of lipases and esterases which are contained in the humor such as serum, urine and pancreatic juice.

As the methods for measuring activities of lipases, there have been known, for example, methods using an olive oil as the substrate. Such methods include a method which comprises bringing the sample into contact with the olive oil and conducting alkali titration of the isolated fatty acids and a method which comprises measuring, as an index, the change of the temperature in the olive oil emulsion. However, these methods have some defects, for example, in that in these methods, the measurement values change and reproducibility becomes unsatisfactory depending on the difference in the quality of the olive oil as the starting substance and the difference in the way of preparation of emulsions.

The methods for measuring lipase activities which comprise using α-naphthyl palmitate as the substrate have some problems, for example, that it is impossible to add the substrate in an amount enough to measure the enzyme activities since the substrate is sparingly soluble, that the measurement values vary depending upon the difference in the way of preparing the substrate solution, and that their reproducibility is inferior.

The methods for measuring lipase activities with the use of a synthetic thioester, 2,3-dimercaptopropan-1-ol tributylate (BALB), as the substrate are widely used since their reproducibility and accuracy are relatively better. However, they also have some problems, for example, that the fatty acid ester as the substrate has a short chain and the substrate is hydrolized not only by lipases but also by esterases, and thus the methods lack substrate specificity. Besides, the methods have other defects that since they need a reaction-terminating liquid, they involve complicated procedures and rate assay methods which are considered the most suitable for the measurement of enzyme activities cannot be applied to the method.

In the methods for measuring esterase activities, there are some defects, for example, that it is impossible to add the substrate in an amount enough to measure enzyme activities since the substrate is sparingly soluble, that the measurement values vary in accordance with the way of preparation of the solution of the substrate and that their reproducibility is inferior.

The object of the present invention is to solve the above-mentioned problems and overcome the defects. The primary object is to provide compounds useful as substrates which are free of variation depending on the quality of the starting substances, have a definite structure and have an excellent solubility.

The second and the third objects are to provide reagents for the measurement of lipase or esterase activities and to provide methods for measuring said activities which are excellent in reproducibility and sensitivity and which permit the measurement by rate-assay method by a simple procedure.

DESCRIPTION OF THE INVENTION

The present invention relates to the following (1) to (3).

(1) Sugar ester derivatives of the general formula (I) [hereinafter referred to as sugar ester derivatives (I)]

wherein G stands for a group of the formula (A)

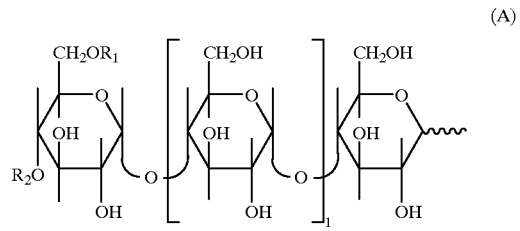

or a group of the formula (B)

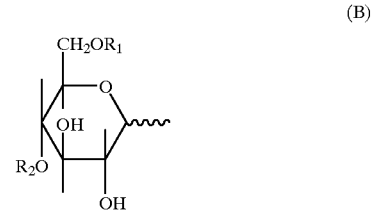

wherein $\lambda$ means 0 or 1; at least one of $R_1$ and $R_2$ means an ester residue of a saturated or unsaturated fatty acid having 1–30 carbon atoms and the other group means hydrogen atom or acetyl group, and $R_3$ means a group of the formula (C)

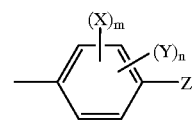

wherein X means a halogen atom, m means an integer of 0 to 4, Y means hydroxy group, an alkoxy group, a carboxyl group or sulfonic acid group, n means 0 or 1 and Z means nitro group or nitrovinyl group.

(2) Reagents for the measurement of lipase or esterase activities characterized by containing said sugar ester derivative (I) as the substrate.

(3) Methods for measuring lipase or esterase activities which comprise allowing the sample to act on said sugar ester derivative (I) as the substrate in the presence of at least one auxiliary enzyme selected from among α-glucosidase, glucoamylase and α-glucosidase and measuring the isolated phenol compound.

That is, the present invention is concerned with sugar ester derivatives (I) which are 4-nitrophenyl- or 4-(nitrovinyl) phenyl-α-glucosides or maltooligosides in which the hydroxyl group(s) at the 4-position and/or 6-position of the non-reductive terminal glucose is modified, and/or 4-nitrophenyl- or 4-(nitrovinyl)phenyl-6-glucosides or maltooligosides in which the hydroxyl group(s) at the 4-position and/or at the 6-position of the non-reductive terminal glucose is modified, reagents which comprise said sugar ester derivative (I) as the substrate and methods for measuring lipase or esterase activities with said reagents.

The maltooligosaccharide which constructs the frame of the sugar ester derivative (I) of the present invention consists of 2 to 3 sugar(s) [See the formulae (A)].

As the maltooligosaccharide, preferable are maltose and maltotriose.

The substitients $R_1$ and $R_2$ of glucoside or the non-reductive terminal glucose of maltooligosaccharide may be the same or different. When either of $R_1$ and $R_2$ is a fatty acid ester residue having not less than 5 carbon atoms, preferably the glucoside maltooligosaccharide is used as the substrate for the measurement of lipase activities, and when both of $R_1$ and $R_2$ are fatty acid ester residues having not more than 5 carbon atoms, preferably the glucoside or maltooligosaccharide is used as the substrate for the measurement of esterase activities.

Referring to $R_1$ and $R_2$, the fatty acid ester residue may be saturated or unsaturated and may be straight-chain or branched.

As the fatty acid esters formed by said fatty acid ester residues, mention is made of stearolic acid ester, arachidonic acid ester, linolenic acid ester, linoleic acid ester, sorbic acid ester, brassidic acid ester, erucic acid ester, cetoleic acid ester, elaidic acid ester, oleic acid ester, undecylenic acid ester, heptacosanoic acid ester, pentacosanoic acid ester, cerotic acid ester, lignoceric accid ester, behenic acid ester, arachidic acid ester, nonadecanoic acid ester, stearic acid ester, heptadecanoic acid ester, palmitic acid ester, pentadecanoic acid ester, myristic acid ester, tridecanoic acid ester, lauric acid ester, undecylic acid ester, capric acid ester, pelargonic acid ester, caprylic acid ester, enanthic acid ester, caproic acid ester, valeric acid ester, butyric acid ester, propionic acid ester, acetic acid ester, formic acid ester, isocrotonic acid ester, crotonic acid ester, acrylic acid ester and the like.

$R_3$ which is an aglycon of the modified glucoside or maltooligoside is a group represented by the above-mentioned formula (C).

Referring to X in the formula (C), the halogen includes fluorine atom, chlorine atom, bromine atom and iodine atom, preferably fluorine atom or chlorine atom and m is an integer of 0 to 4.

Y in the formula (C) stands for hydroxy group, an alkoxy group, carboxyl group or sulfonic acid group and n is 0 or 1.

Referring to Y, the alkoxy group may be straight or branched, preferably a lower alkoxy group having 1 to 4 carbon atoms, which is specifically exemplified by methoxy, ethoxy, n-propoxy, iso-propoxy, n-butoxy and so on.

$R_3$ may be attached to the hydroxy group at the 1-position of the non-reductive terminal glucose in the α-type or in the β-type.

The phenyl groups having the formula represented by the formula (C) are, in other words, nitro or nitrovinyl phenol residues. As the preferred substituted phenols which form said groups, mention is made of, for example, 4-nitrophenol, 2-chloro-4-nitrophenol, 2-fluoro-4-nitrophenol, 2-bromo-4-nitrophenol, 2-iodo-4-nitrophenol, 2,6-dichloro-4-nitrophenol, 2,6-difluoro-4-nitrophenol, 2,6-dibromo-4-nitrophenol, 2,6-diiodo-4-nitrophenol, 2,3-difluoro-4-nitrophenol, 2,5-difluoro-4-nitrophenol, 2,3,6-trifluoro-4-nitrophenol, 4-(2'-nitrovinyl) phenol, 2-methoxy-4-(2'-nitrovinyl)phenol, 2-hydroxy-4-(2'-nitrovinyl) phenol, 2-fluoro-4-(2' -nitrovinyl)phenol, 2-chloro-4-(2'-nitrovinyl) phenol, 2-bromo-4-(2'-nitrovinyl)-phenol, 2-iodo-4-(2'-nitrovinyl)phenol, 2,6-difluoro-4-(2'-nitrovinyl) phenol, 2,6-dichloro-4-(2'-nitrovinyl)phenol, 2,6-dibromo-4-(2'-nitrovinyl) phenol, 2,6-diiodo-4-(2'-nitrovinyl)phenol and the like.

The above-mentioned sugar ester derivatives (I), that is, modified 4-nitrophenyl- or 4-(nitrovinyl)phenyl-α(or β)-glucosides or maltooligosides are novel compounds. As the preferred ones of such compounds, mention can be made of, for example, the following compounds.

The following compounds are sometimes referred to briefly as shown respectively in the brackets [ ].

(1) 2-Fluoro-4-nitrophenyl 6-O-oleoyl-β-D-glucopyranoside [Oleoyl 2-fluoro-4-nitrophenyl-β-glucopyranoside]

(2) 4-Nitrophenyl 6-O-palmitoyl-α-D-glucopyranoside [Palmitoyl 4-nitrophenyl-α-glucopyranoside]

(3) 4-Nitrophenyl 4-O-acetyl-6-O-linoloyl-O-α-D-glucopyranosyl-(1→4) -α-D-glucopyranoside [4-Acetyl-6-linoloyl-4-nitrophenyl-α-maltoside]

(4) 2,3-difluoro-4-nitrophenyl 6-O-lauroyl-O-α-D-glucopyranosyl-(1→4) -β-D-glucopyranoside [6-Lauroyl 2,3-difluoro-4-nitrophenyl-β-maltoside]

(5) 2-Methoxy-4-(2'-nitrovinyl)phenyl 6-O-acetyl-β-D-glucopyranoside [Acetyl 2-methoxy-4-(nitrovinyl)phenyl-β-glucopyranoside]

(6) 4-Nitrophenyl 4,6-O-diacetyl-O-α-D-glucopyranosyl-(1→4) -α-D-glucopyranoside [Diacetyl 4-nitrophenyl-α-maltoside]

(7) 2-Chloro-4-nitrophenyl 6-O-acetyl-O-β-D-glucopyranoside [Acetyl 2-chloro-4-nitrophenyl-β-glucopyranoside]

(8) 4-Nitrophenyl 6-O-pentanoyl-O-α-D-glucopyranoside [Pentanoyl 4-nitrophenyl-α-glucopyranoside]

(9) 4-Nitrophenyl 4,6-D-dipentanoyl-O-α-D-glucopyranoside [dipentanoyl 4-nitrphenyl-α-glucopyranoside]

(10) 2-Fluoro-4-nitrophenyl 6-O-butyroyl-O-β-D-glucopyranoside [Butyroyl 2-fluoro-4-nitrophenyl-β-glucopyranoside]

The sugar ester derivatives (I) of the present invention can be produced, for example, by allowing the above-mentioned phenols (the aglycon) to form an O-glycoside-bond at the reductive terminus of the glucosides or maltooligosaccharides (e.g. maltose, maltotriose) in the α-type or β-type by a per se known method, followed by selective esterification of the hydroxy group(s) at the 6-position and/or at the 4-position alone of the non-reductive terminal glucose with the fatty acid or a reactive derivative thereof corresponding to $R_1$ and $R_2$ by a per se known method.

The methods for bonding said phenols (aglycon) in the α-type can be usually carried out by Helferich method [Methods in Carbohydrate Chemistry, vol. II, p. 345 (1963) or Bull. Chem. Soc. Jpn., 54, 1985 (1981)] or the methods analogous thereto. The methods for bonding in the β-type can be conducted by polyacylglycosyl halide method [Angew. Chem., 86 173 (1974)] or the methods analogous thereto.

As the esterification reaction of the sugar hydroxyl groups (the hydroxy groups at the 6-position and/or at the 4-position of the non-reductive terminal glucose) with said fatty acids or their reactive derivatives, chemical synthetic methods or enzymatic synthetic methods can be usually adopted. Preferably selective synthetic methods by enzymes can be used. In the methods, lipases are preferably used. As the lipases to be used for said reactions, any lipases can be used so long as they are capable of allowing the sugar hydroxy groups and said fatty acids to form monoesters. As the specific examples of such lipases, mention is made of lipases from microorganisms belonging to genus Pseudomonas and genus Chromobacterium. More specifically, there may be mentioned lipases from *Pseudomonas fluorescens, Pseudomonus fragi* and *Chromobacterium viscosum*. As the marketed products of these lipases, there are Lipase P (manufactured by Amano Pharmaceutical Inc.), Lipase B (manufactured by Sapporo Breweries Limited), Lipase LP (manufactured by Toyo Jozo Co., Ltd.). Usually these marketed products can be used. The enzymatic reactions are usually conducted at 20–30° C. It is preferable to conduct the reactions while shaking or stirring in order that the enzymes may be properly dispersed throughout the reaction systems. After the completion of the reactions, the enzymes are collected by filtration and can be used repeatedly. As the reaction solvents, organic solvents are more preferable than aqueous solvents. Any dry organic solvent can be used, and preferably use is made of, for example, acetone, dioxane, diethyl ether, pyridine and hexane. Though numerous esterification reactions by enzymes in organic solvents have been so far known [e.g. Proc. Natl. Acad. Sci. USA., 82, 3192 (1985)], ester-exchange reactions using fatty acid esters are preferably adopted for the present invention. As such fatty acid esters, preferred are high hydropholic esters, which are exemplified by vinyl esters, phenyl esters, tributyrylsters, trichloroethyl esters and the like.

The production of the diesters at the 4- and 6-positions can be conducted in the following manner. That is, first, dihydroxy compounds having a primary hydroxy groups at the 6-position and a secondary hydroxy group at the 4-position can be produced by conducting selective acetalation of the 4- and 6-positions alone of the non-reductive terminal glucose of sugar derivatives modified at the reductive terminus and removing the acetal at the termini with the other hydroxy groups protected with a protective group other than acyl groups. By converting the dihydroxy compounds into their monoesterified compounds of the primary hydroxy group at the 6-position by one of the above-mentioned enzymatic esterification methods, followed by esterification of the hydroxy group at the 4-position by a chemical synthetic method and removal of the protective groups, the diester compounds at the 4- and 6-positions can be produced. The acetalation at the termini proceeds, via the acetal compound with benzylidene or isopropylidene bonded to the 4- and 6-positions thereof, by, for example, reacting benzaladehyde, acetone and the like in the presence of a Lewis acid. As the protective groups other than acyl groups, mention may be made of, for example, benzyl ether, allyl ether, methoxy methyl ether and p-bromophenacyl ether.

The reagents of the present invention, as mentioned above, enable the measurement of lipase and esterase activities by allowing the sample containing a lipase or an esterase to act on a sugar ester derivative (I) as the substrate in the presence of at least one auxiliary enzyme selected from among α-glucosidase, glucoamylase and/or β-glucosidase and measuring the isolated phenol compound.

Accordingly, the reagents of the present invention contain the above-mentioned sugar ester derivatives (I) as the substrates, and they usually further contain an auxiliary enzyme system which comprises α-glucosidases, glucoamylases, and/or β-glucosidases singly or in combination and, if necessary, other additives.

The origins of α-glucosidases, β-glucosidases and glucoamylases to be used for said measurement are not limited.

For example, preferably used are α-glucosidases originated from yeasts, β-glucosidases obtained from almond and glucoamylases obtained from *Rhizopus delemar*.

For example, when a substrate in which the aglycon is bonded in the α-type (α-type substrate) is used, use is made of an α-glucosidase solely or a combination of an α-glucosidase and a glucoamylase as the auxiliary enzymatic system. When a substrate in which the aglycon is bonded in the β-type (β-type substrate) is used, use can be made of a β-glucosidase alone, a combination of an α-glucosidase and a β-glucosidase or a combination of an α-glucosidase, a glucoamylase and a β-glucosidase as the auxiliary enzymatic system.

The mixture of sugar ester derivative in which aglycon is bonded in α-type and sugar ester derivative in which aglycon is bonded in β-type may be used as substrates.

Preferably, in the reagents of the present invention are incorporated activating agents for lipases and esterases and stabilizing agents such as colipase, cholates, magnesium salts and calcium salts.

Additionally, there may be added buffer agents, surfactants, antiseptics and the like.

There may be added inhibitors of the esterase in the measurement of the lipase or inhibitors of the lipase in the measurement of the esterase.

The reaction formulae of the substrates in the measurement of lipase and esterase activities using the reagents of the present invention are explained with 4-acetyl-6-linoloyl 4-nitrophenyl-α(or β)-maltoside taken as an example.

(1) In the case where 4-acetyl-6-linoloyl 4-nitrophenyl-α-maltoside is used as the substrate:

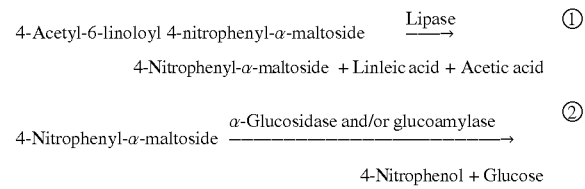

(2) In the case where 4-acetyl-6-linoloyl 4-nitrophenyl-β-maltoside is used as the substrate:

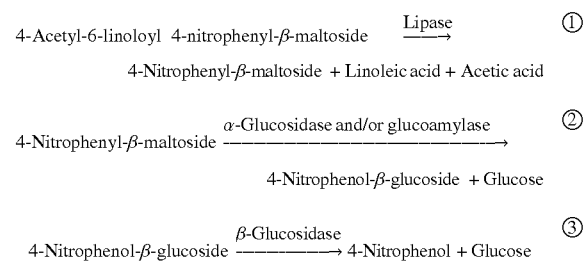

By measuring the phenol compounds isolated in the above reactions (in the above-mentioned example, 4-nitrophenol) by a suitable means, the lipase activities can be measured. When the isolated phenol compounds show spectrum absorption different from the substrates, the spectra of the reaction mixture are directly measured. When the phenol compounds isolated from the substrates show almost the same spectrum absorption, the phenol compounds are subjected to oxidative condensation with a coloring agent, e.g. a coloring matter such as 4-aminoantipyrine and hydrogen peroxide in the presence of peroxidase, and the coloring intensity is measured.

The present invention can be put into use as a two-liquid type reagent in which the substrate [a sugar ester derivative (I)] and the auxiliary enzyme are separated and as a one-liquid type reagent in which the substrate and the auxiliary enzyme are combined.

Below, the present invention is explained specifically by illustrating working Examples.

EXAMPLE 1
Synthesis of 2-fluoro-4-nitrophenyl 6-O-oleoyl-β-D-glucopyranoside:

(1) In 60 ml of chloroform were dissolved 7.66 g (18.6 mmol) of tetra-O-acetyl-α-D-glucopyranosyl bromide [M. Barczai-Martos, Nature, 165, 369 (1950)], 2.69 g (17.12 mmol) of 2-fluoro-4-nitrophenol and 1.8 g of triethylbenzylammonium bromide, and 8.5 ml (17 mmol) of a 2N-aqueous solution of sodium hydroxide was added dropwise to the mixture under vigorous stirring in an oil bath at 60° C. The mixture was reacted as it was for 3 hours. After cooling, 80 ml of water was added to the reaction mixture, and the mixture was extracted with dichloromethane. The organic layer was dried and concentrated to give 6.5 g of a yellow-red oil. Addition of 1 ml of methanol crystallized needle crystals, which were recrystallized from a mixed solvent of ether-methanol (1:1) to give 5.0 g of 2-fluoro-4-nitrophenyl-2,3,4,6-tetra-O-acetyl-β-D-glucopyranoside. Yield 60%

(2) In 80 ml of anhydrous methanol was suspended 3.6 g (7.38 mmol) of the above-mentioned product, and to the suspension was added dropwise 4.0 ml (2.0 mmol) of a 0.5 N-sodium methoxide-methanol solution under stirring at room temperature. After the mixture was stirred for 15 minutes, 4 ml of Amberlyst® 15 (H⁺ type), cation exchange resin, was added to the obtained pale-yellow solution. The mixture was stirred at room temperature for 30 minutes. Said exchange resin was filtered off and washed with methanol. The filtrate and the washing liquid were combined and concentrated under reduced pressure to give white crystals, which was further recrystallized from ethanol to give 2.28 g of 2-fluoro-4-nitrophenyl-β-D-glucopyranoside as white needle crystals. Yield 97%

(3) In 40 ml of acetone were suspended 0.32 g (1 mmol) of the above-mentioned product, 1.075 g (3 mmol) of phenyl ester of oleic acid and 30 mg of Lipase B (manufactured by Sapporo Breweries Limited). The mixture was reacted in a shaking apparatus at 25° C. for 1 day.

After the enzyme was filtered off, the filtrate was concentrated to give a crude product in a white wax form. This crude product was purified by silica gel (Merck Inc.) column chromatography (5% methanol-dichloromethane) to give 0.52 g of 2-fluoro-4-nitrophenyl 6-O-oleoyl-β-glucopyranoside. Yield 79%

The physicochemical properties of this product are as shown below.

IR: $\nu_{max}^{KBr}$ 3460, 2925, 2850, 1730, 1530, 1350, 1290, 1080 cm$^{-1}$ $^1$H-NMR: $\delta_{CD3OD}^{TMS}$ (400 MHz-NMR)

0.88 (t, 3 H), 1.25 (m, 22 H), 1.57 (m, 2 H), 1.99 (m, 4 H), 3.39 (t, 1 H, J=9.7 Hz: $C_4$—H), 3.53 (m, 2 H: $C_2$ and $C_3$—H), 3.73 (dt, 1 H, J=9.5, 2 Hz: $C_5$—H), 4.22 (dd, 1 H, J=12, 7 Hz: $C_6$—H), 4.44 (dd, 1 H, J=12, 2 Hz: $C_6$—H), 5.16 (d, 1 H, J=7,5 Hz: $C_1$—H, β type), 7.41 (t, 1 H, J=9 Hz), 8.06 (d, 2 H, J=9 Hz) ppm $[\alpha]_D^{24}$=-64,9° (methanol, c=0.13)

UV=$\lambda_{max}$ 295 nm (methanol)

EXAMPLE 2
Synthesis of 4-nitrophenyl 6-O-palmitoyl-α-D-glucopyranoside:

In 40 ml of acetone were suspended 0.3 g (1 mmol) of 4-nitrophenyl-α-D-glucopyranoside (manufactured by Tokyo Kasei Ind., Ltd.) as marketed, 0.85 g (3 mmol) of vinyl palmitate and 30 mg of Lipase B, and the suspension was reacted in a shaking apparatus at 25° C. for 1 day. After the enzyme was filtered off, the solvent was concentrated to afford a crude product in a white wax form, which was purified by silica gel chromatography (5% methanol-dichloromethane) to give 0.458 g of 4-nitrophenyl 6-O-palmitoyl-α-D-glucopyranoside in a white wax form. Yield 81%

The physicochemical properties of this product are shown below.

IR: $\nu_{max}^{KBr}$ 3550, 3050, 1720, 1360 cm$^{-1}$ $^1$H-NMR: $\delta_{CD3OD}^{TMS}$ (400 MHz-NMR)

0.88 (t, 3 H), 1.256 (m, 24 H), 1.56 (m, 2 H), 2.26 (t, 2 H), 3.42 (dd, 1 H, J=9, 1 Hz: $C_4$—H), 3.69 (dd, 1 H, J=10, 4 Hz: $C_2$—H), 3.77 (m, 1 H: $C_5$—H), 3.89 (dd, 1 H, J=10, 1 Hz: $C_3$—H), 4.29 (m, 2 H: $C_6$—H), 5.62 (d, 1 H, J=3.7 Hz: $C_1$—H αtype), 7.22 (d, 2 H, J=9 Hz), 8.21 (d, 2 H, J=9 Hz) ppm $[\alpha]_D^{24}$=+109.1° (methanol, c=0.10)

UV=$\lambda_{max}$ 295 nm (methanol)

EXAMPLE 3
Synthesis of 4-nitrophenyl 4-O-acetyl-6-O-linoloyl-O-α-D-glucopyranosyl-(1→4) -α-D-glucopyranoside (1) A flask was charged with 0.1 g (0.2 mmol) of p-nitrophenyl-α-maltoside as marketed, 0.1 g (0.65 mmol) of (dimethoxymethyl)benzene, 10 ml of dimethylformamide and 10 mg of p-toluenesulfonic acid-hydrate, and a rotary-evaporator was equipped with the flask, which was rotated under reduced pressure in a water-bath at 60° C. for 1 hour. Thereafter, the temperature of the water-bath was elevated to 100° C. under reduced pressure, and DMF was distilled off. To the thus-obtained crude product was added 10 ml of sodium hydrogen carbonate, and the pale-yellow insoluble matter (the corresponding 4,6-O-benzylidene derivative) was filtered off. 96 mg, Yield 83%

(2) In 30 ml of benzene were dissolved 90 mg of said product, 200 mg of methoxymethyl chloride and 10 mg of diisopropylethylamine, and the solution was stirred at room temperature for 6 hours. After the solvent was concentrated, the crude product was purified by silica gel chromatography. The obtained purified product was subjected to hydrogenation with 5% palladium-carbon catalyst in methanol, and the product was purified by silica gel chromatography to give 101 mg of the corresponding 4,6-dihydroxy compound (a colorless oil).

(3) The above-mentioned product (90 mg) was converted into the corresponding 6-O-linoloyl derivative with Lipase B in accordance with Example 1(3). The obtained crude product was dissolved in a mixture of pyridine-acetic anhydride (2 ml), and the solution was reacted at room temperature overnight. After the removal of the solvent, the obtained crude product was dissolved in 5 ml of acetic acid, followed by addition of a drop of conc. sulfuric acid at 0° C. The mixture was stirred for 5 minutes. After neutralization, the mixture was concentrated and purified by silica gel column chromatography (8% methanol-dichloromethane) to give 25 mg of 4-nitrophenyl 4-O-acetyl-6-O-linoloyl-O-α-D-glucopyranosyl-(1→4) -α-D-glucopyranoside in a white wax form.

The physicochemical properties of this product are shown below.

IR: $\nu_{max}^{KBr}$ 3430, 2920, 2850, 1716, 1600, 1510, 1350 cm$^{-1}$ $^1$H-NMR: $\delta_{CD3OD}^{TMS}$ 0.8–2.2 (m, 27 H), 2.0 (s, 3 H), 3.2–4.7 (m), 5.2 (d, 1 H, J=3.8 Hz), 5.7 (d, 1 H, J=3.7 Hz), 7.2 (d, 2 H, J=7 Hz), 8.2 (d, 2 H, J=9 Hz) ppm $[\alpha]_D^{24}$=+61° (methanol, c=0.09)

UV=$\lambda_{max}$ 295 nm (methanol)

EXAMPLE 4

Synthesis of 2,3-difluoro-4-nitrophenyl 6-O-lauroyl-O-α-D-glucopyranosyl-(1→4)-β-D-glucopyranoside (1) In 50 ml of dichloromethane were dissolved 5.0 g (7.1 mmol) of maltoside bromide, 2.3 g (14 mmol) of 2,3-difluoro-4-nitrophenol and 1.5 g of triethylbenzylammonium chloride, and 3.8 ml (7.6 mmol) of a 2N-aqueous solution of sodium hydroxide was added dropwise to the solution under vigorous stirring in an oil-bath at 40° C. The mixture was reacted for 5 hours. After 100 ml of water was added to the reaction mixture, the mixture was extracted with dichloromethane. The organic layer was dried and concentrated to give a reddish brown oil, which was purified by silica gel column chromatography and recrystallized from ethanol to give 3.3 g of 2,3-difluoro-4-nitrophenyl-O-peracetyl-β-maltoside as white crystals. Yield 60%

(2) In 80 ml of anhydrous methanol was suspended 3.0 g (3.8 mmol) of said product, and to the suspension was added dropwise 3.0 ml (1.5 mmol) of 0.5N-sodium methoxide-methanol solution under stirring at room temperature. After the mixture was stirred for 15 minutes, 4 ml of Amberlyst®15 (H$^+$ type), a cation exchange resin, was added to the pale-yellow solution and the mixture was stirred for 30 minutes. The exchange resin was filtered off and washed with methanol. The filtrate and washings were combined and concentrated under reduced pressure to give white crystals, which were recrystallized from ethanol to give 2.1 g of 2,3-difluoro-4-nitrophenyl-β-maltoside as white crystals. Yield 90%

(3) In 40 ml of dioxane were suspended 0.46 g (1 mmol) of said product, 0.68 g (3 mmol) of vinyl laurate and 30 ml of Lipase B, and the suspension was reacted in a shaking apparatus at 25° C. for 1 day. After the enzyme was filtered off, the solvent was concentrated to give a crude product in a white wax form, which was purified by silica gel column chromatography to give 0.35 g of 2,3-difluoro-4-nitrophenyl 6-O-lauroyl-O-α-D-glucopyranosyl-(1→4)-β-D-glucopyranoside. Yield 50%

The physicochemical properties of this compound are shown below.

IR: $\nu_{max}^{KBr}$ 3450, 3130, 3100, 1730, 1530, 1290, 1080 cm$^{-1}$ $^1$H-NMR: $\delta_{CD3OD}^{TMS}$ 0.9 (t, 3 H), 1.3 (m, 16 H), 1.5 (m, 2 H), 2.3 (m, 2 H), 3.2–4.7 (m), 5.2 (d, 1 H, J=4 Hz), 5.7 (d, 1 H, J=8 Hz), 7.3 (t, 1 H), 8.0 (t, 1 H) ppm $[\alpha]_D^{24}$=−69.0° (methanol, c=0.10)

UV=$\lambda_{max}$ 298 nm (methanol)

EXAMPLE 5

A reagent having the following formulation was prepared.

| Reagent Formulation A: | |
|---|---|
| 50 mM Good buffer | (pH8.5) |
| Sodium cholate | 0.1% |
| β-Glucosidase | 100 U/ml |
| Oleoyl 2-fluoro-4-nitrophenyl-β-glucopyranoside | 1 mM |
| Reagent Formulation B: | |
| 50 mM Good buffer | (pH8.5) |
| Sodium cholate | 0.1% |
| α-Glucosidase | 50 U/ml |
| Palmitoyl 4-nitrophenyl-α-glucopyranoside | 1 mM |
| Reagent Formulation C: | |
| 50 mM Good buffer | (pH8.5) |
| Sodium cholate | 0.1% |
| α-Glucosidase | 100 U/ml |
| 4-Acetyl-6-linoloyl-4-nitrophenyl-α-maltoside | 1 mM |
| Reagent Formulation D: | |
| 50 mM Good buffer | (pH8.5) |
| Sodium cholate | 0.1% |
| α-Glucosidase | 100 U/ml |
| Glucoamylase | 10 U/ml |
| β-Glucosidase | 50 U/ml |
| β-Lauroyl 2,3-difluoro-4-nitrophenyl-β-maltoside | 1 mM |

Using these reagents, lipase activities were measured.

Said reagents (3 ml each) were added to 100 μl of (1) pancreatic lipase solution and (2) serum sample, and the mixtures were left standing still at 37° C. for 4–5 minutes. Thereafter, change in absorbance per minute (as the index of lipase activity) was estimated by measuring change in adsorbance at 400 nm. Change in the reagent blank value with the lapse of time and change in absorbance per minute are shown in Table 1. (In the blank, water was used instead of samples.)

TABLE 1

| Reagent | Change in blank value | Pancreatic lipase | Serum |
|---|---|---|---|
| A | 0.002 | 0.026 | 0.014 |
| B | 0.001 | 0.028 | 0.018 |
| C | 0.002 | 0.025 | 0.014 |
| D | 0.002 | 0.029 | 0.015 |

The reagents A, B, C and D of the present invention show little change in blank and have measurement sensitivity enough to measure lipase activities in samples.

EXAMPLE 6

Synthesis of 2-methoxy-4-(2'-nitrovinyl)phenyl 6-O-acetyl-β-D-glucopyranoside (1) In accordance with Example 1, 2.0 g (4.8 mmol) of tetra-O-acetyl-α-D-glucosyl bromide, 0.9 g (5.9 mmol) of O-vaniline and 0.5 g of triethylbenzylammonium bromide were dissolved in 25 ml of chloroform, and 5 ml (5 mmol) of a 1N-aqueous solution of sodium hydroxide was added dropwise to the mixture under vigorous stirring at room temperature. The mixture was reacted overnight. Water (50 ml) was added to the reaction mixture, and the mixture was extracted with dichloromethane. The organic layer was dried and concentrated to give a pale-yellow oil. The oil was left standing still to be crystallized. The crystals were recrystallized from an aqueous solution of acetone to give 1.4 g of 2-methoxy-4-formylphenyl-2,3,4,6-tetra-O-acetyl-β-D-glucopyranoside as white crystals. Yield 60%

(2) In 50 ml of methanol was suspended 0.96 g (2 mmol) of said product, and 1 ml (0.5 mmol) of a 0.5 N sodium methoxide-methanol solution was added dropwise thereto under stirring at room temperature. Fifteen minutes later, 2 ml of Amberlyst®15 (H⁺ type) was added, and the mixture was reacted for 30 minutes. The exchange resin was filtered off, and washed with methanol. The filtrate and the washings were combined and concentrated under reduced pressure to give 0.58 g of white crystals. Yield 92%

(3) Said product [0.31 g (1 mmol)] was suspended in 10 ml of methanol, and 1.2 ml of nitromethane, 0.2 ml of acetic acid and 0.2 g of ammonium acetate were added to the suspension. The mixture was heated under reflux for 30 minutes. After cooling, pale-yellow crystals were deposited to give 0.3 g (85%) of 2-methoxy-4-(2'-nitrovinyl)phenyl-β-D-glucopyranoside.

(4) In 40 ml of acetone were suspended 0.34 g (1 mmol) of said product, 0.34 g (4 mmol) of vinyl acetate and 30 mg of Lipase B, and the suspension was reacted in a shaking apparatus at 25° C. for 1 day. The enzyme was filtered off, and the filtrate was concentrated, followed by crystallization from ethanol to give 200 mg of pale-yellow 2-methoxy-4-(2'-nitrovinyl)phenyl 6-O-acetyl-β-D-glucopyranoside. Yield 52%

The physicochemical properties of this compound are shown below.

$^1$H-NMR: $\delta_{CD3OD}^{TMS}$ 2.03 (s, 3 H), 3.3–3.9 (m, 4 H), 3.8 (s, 3 H), 4.3 (m, 2 H), 5.4 (d, 1 H, J=8 Hz), 7.0 (d, 1 H, J=9 Hz), 7.44 (dd, 1 H), 7.5 (d, 1 H, J=14 Hz), 7.7 (d, 1 H), 7.9 (d, 1 H, J=14 Hz)

EXAMPLE 7

The reagents having the following formulations were prepared.

| Reagent Formulation A: | |
| --- | --- |
| 50 mM Good buffer | (pH8.0) |
| Sodium cholate | 0.1% |
| β-Glucosidase | 100 U/ml |
| Acetyl 2-methoxy-4-(nitrovinyl)-phenyl-β-glucopyranoside | 1 mM |
| Reagent Formulation B: | |
| 50 mM Good buffer | (pH8.0) |
| Sodium cholate | 0.1% |
| α-Glucosidase | 100 U/ml |
| Diacetyl 4-nitrophenyl-α-maltoside | 1 mM |
| Reagent Formulation C: | |
| 50 mM Good buffer | (pH8.0) |
| Sodium cholate | 0.1% |
| α-Glucosidase | 100 U/ml |
| Acetyl 2-chloro-4-nitrophenyl-β-Glucopyranoside | 1 mM |
| Reagent Formulation D: | |
| 50 mM Good buffer | (pH8.0) |
| Sodium cholate | 0.1% |
| α-Glucosidase | 100 U/ml |
| Pentanoyl 4-nitrophenyl-α-glucopyranoside | 1 mM |
| Reagent Formulation E: | |
| 50 mM Good buffer | (pH8.0) |
| Sodium cholate | 0.1% |
| α-Glucosidase | 100 U/ml |
| Dipentanoyl 4-nitrophenyl-α-glucopyranoside | 1 mM |
| Reagent Formulation F: | |
| 50 mM Good buffer | (pH8.0) |
| Sodium cholate | 0.1% |
| β-Glucosidase | 100 U/ml |
| Butyroyl 2-fluoro-4-nitrophenyl-β-glucopyranoside | 1 mM |

Esterase activities were measured with the use of these reagents. The above-mentioned reagents (each 3 ml) were added to 100 μl of (1) carboxyesterase samples and (2) serum samples, and the mixtures were left standing at 37° C. for 4–5 minutes. Thereafter, by measuring change in adsorbance at 400 nm, change in adsorbance per minute (as the index for esterase activities) was estimated. Change in blank value of samples with the lapse of time and change in adsorbance per minute are shown in Table 2. (In blank, water was used instead of samples.)

TABLE 2

| Reagent | Change in blank value | Carboxyesterase | Serum |
| --- | --- | --- | --- |
| A | 0.003 | 0.043 | 0.014 |
| B | 0.002 | 0.037 | 0.011 |
| C | 0.004 | 0.041 | 0.013 |
| D | 0.003 | 0.035 | 0.010 |
| E | 0.002 | 0.033 | 0.009 |
| F | 0.003 | 0.029 | 0.007 |

Reagents A, B, C, D, E and F of the present invention show small change in blank and have measurement sensitivity enough to measure esterase activities in samples.

The substrates of the present invention have effects since that they have a definite structure since $R_1$ and/or $R_2$ in the formula (I) are a specific fatty acid ester residue, that they show little change depending on the starting substance and that they have excellent solubility in water.

The measurement with the reagents of the present invention can be continually conducted with the use of autoanalyzer and permits simple and inexpensive measurement of lipase and esterase activities.

What is claimed is:

1. A sugar ester of fatty acid represented by the formula (I)

$$G \sim O - R_3 \qquad (I)$$

wherein G stands for a group of the formula (A)

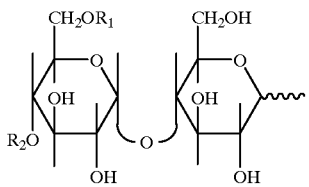
(A)

or a group of the formula (B)

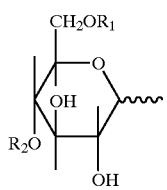
(B)

wherein at least one of $R_1$ and $R_2$ means an ester residue of a saturated or unsaturated fatty acid having 5–30 carbon atoms and the remainder means hydrogen atom or acetyl group and $R_3$ means a group of the formula (C)

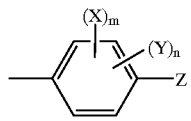
(C)

wherein X means a halogen atom, m means an integer of 0 to 4, Y means hydroxy group, an alkoxy group, a carboxyl group or sulfonic acid group, n means 0 or 1 and Z means nitro group or nitrovinyl group.

2. A compound as claimed in claim 1 which is selected from among the following compounds:

(1) 2-Fluoro-4-nitrophenyl 6-O-oleoyl-β-D-glucopyranoside [Oleoyl 2-fluoro-4-nitrophenyl-β-glucopyranoside]

(2) 4-Nitrophenyl 6-O-palmitoyl-α-D-glucopyranoside [Palmitoyl 4-nitrophenyl-α-glucopyranoside]

(3) 4-Nitrophenyl 4-O-acetyl-6-O-linoloyl-O-α-D-glucopyranosyl-(1→4)-α-D-glucopyranoside [4-Acetyl-6-linoloyl-4-nitrophenyl-α-maltoside]

(4) 2,3,-difluoro-4-nitrophenyl 6-O-laurolyl-O-α-D-glucopyranosyl-(1→4)-β-D-glucopyranoside [6-Laurolyl 2,3-difluoro-4-nitrophenyl-β-maltoside]

(5) 4-Nitrophenyl 6-O-pentanoyl-O-α-D-glucopyranoside [Pentanoyl 4-nitrophenyl-α-glucopyranoside]

(6) 4-Nitrophenyl 4,6-D-dipentanoyl-O-α-D-glucopyranoside [Dipentanoyl 4-nitrophenyl-α-glucopyranoside].

3. A reagent for measuring lipase activity which is characterized by containing, as the substrate, a sugar ester of fatty acid represented by the formula (I)

$G \sim O\text{---}R_3$
(I)

wherein G stands for a group of the formula (A)

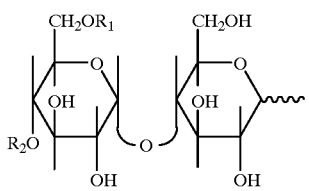
(A)

or a group of the formula (B)

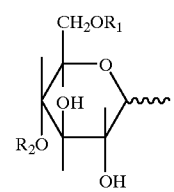
(B)

wherein at least one of $R_1$ and $R_2$ means an ester residue of a saturated or unsaturated fatty acid having 5–30 carbon atoms and the remainder means hydrogen atom or acetyl group and $R_3$ means a group of the formula (C)

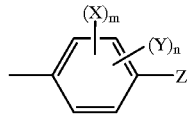
(C)

wherein X means a halogen atom, m means an integer of 0 to 4, Y means hydroxy group, an alkoxy group, a carboxyl group or sulfonic acid group, n means 0 or 1 and Z means nitro group or nitrovinyl group.

4. A reagent for measuring lipase activity comprising a substrate as claimed in claim 3 and an auxiliary enzyme.

5. A reagent for measuring lipase activity as claimed in claim 4 wherein the sugar ester of fatty acid is a compound in which the aglycon is bonded in the α-type, and the auxiliary enzyme is α-glucosidase alone or a combination of α-glucosidase and glucoamylase.

6. A reagent for measuring lipase activity as claimed in claim 4 wherein the sugar ester of fatty acid is a compound in which the aglycon is bonded in the β-type and the auxiliary enzyme is β-glucosidase alone, a combination of α-glucosidase and β-glucosidase or a combination of α-glucosidase, glucoamylase and β-glucosidase.

7. A reagent for measuring lipase activity as claimed in claim 3 in which the sugar ester of fatty acid represented by the formula (I) is selected from among the following compounds:

(1) 2-Fluoro-4-nitrophenyl 6-O-oleoyl-β-D-glucopyranoside [Oleoyl 2-fluoro-4-nitrophenyl-β-glucopyranoside]

(2) 4-Nitrophenyl 6-O-palmitoyl-α-D-glucopyranoside [Palmitoyl 4-nitrophenyl-α-glucopyranoside]

(3) 4-Nitrophenyl 4-O-acetyl-6-O-linoloyl-O-α-D-glucopyranosyl-(1→4)-α-D-glucopyranoside [4-Acetyl-6-linoloyl-4-nitrophenyl-α-maltoside]

(4) 2,3-difluoro-4-nitrophenyl 6-O-lauroyl-O-α-D-glucopyranosyl-(1→4)-β-D-glucopyranoside [6-Lauroyl 2,3-difluoro-4-nitrophenyl-β-maltoside]

(5) 4-Nitrophenyl 6-O-pentanoyl-O-β-D-glucopyranoside [Pentanoyl 4-nitrophenyl-β-glucopyranoside]

(6) 4-Nitrophenyl 4,6-D-dipentanoyl-O-α-D-glucopyranoside [Dipentanoyl 4-nitrophenyl-α-glucopyranoside].

8. A method for measuring lipase activity which comprises allowing a sample to act on a sugar ester of fatty acid represented by the formula (I)

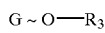   (I)

wherein G stands for a group of the formula (A)

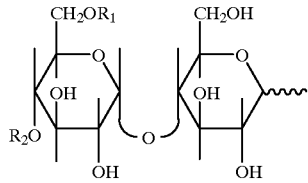   (A)

or a group of the formula (B)

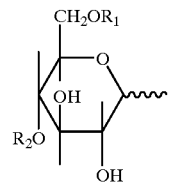   (B)

wherein at least one of $R_1$ and $R_2$ means an ester residue of a saturated or unsaturated fatty acid having 5–30 carbon atoms and the remainder means hydrogen atom or acetyl group, and $R_3$ means a group of the formula (C)

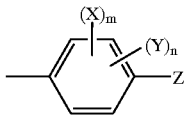   (C)

wherein X means a halogen atom, m means an integer of 0 to 4, Y means hydroxy group, an alkoxy group, a carboxyl group or sulfonic acid group, n means 0 or 1 and Z means nitro group or nitrovinyl group as the substrate in the presence of at least one auxiliary enzyme which is selected from among α-glucosidase, glucoamylase and β-glucosidase and measuring the isolated phenol compound.

* * * * *

UNITED STATES PATENT AND TRADEMARK OFFICE
CERTIFICATE OF CORRECTION

PATENT NO.    : 6,162,614
DATED         : December 19, 2000
INVENTOR(S)   : Minoru Kamimura.

It is certified that error appears in the above-identified patent and that said Letters Patent is hereby corrected as shown below:

<u>Column 15,</u>
Line 7, please amend "β-D-glucopyranoside" should read -- α-D-glucopyranoside --.
Line 8, please amend "β-glucopyranoside" should read -- α-glucopyranoside --.

Signed and Sealed this

Eleventh Day of December, 2001

*Attest:*

NICHOLAS P. GODICI
*Attesting Officer          Acting Director of the United States Patent and Trademark Office*